United States Patent
Watanabe

(10) Patent No.: US 11,959,908 B2
(45) Date of Patent: Apr. 16, 2024

(54) MEASUREMENT DEVICE AND MEASUREMENT METHOD

(71) Applicant: ARKRAY, Inc., Kyoto (JP)

(72) Inventor: Yukio Watanabe, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 656 days.

(21) Appl. No.: 17/123,792

(22) Filed: Dec. 16, 2020

(65) Prior Publication Data

US 2021/0182530 A1 Jun. 17, 2021

(30) Foreign Application Priority Data

Dec. 17, 2019 (JP) ................................. 2019-227645
Dec. 10, 2020 (JP) ................................. 2020-205362

(51) Int. Cl.
*G01N 33/00* (2006.01)
*G01N 15/06* (2006.01)
(Continued)

(52) U.S. Cl.
CPC ........... *G01N 33/493* (2013.01); *G01N 15/06* (2013.01); *G06V 10/20* (2022.01); *G06V 20/69* (2022.01);
(Continued)

(58) Field of Classification Search
CPC ................. G01N 33/493; G01N 15/06; G01N 2015/0065; G01N 2015/0063;
(Continued)

(56) References Cited

U.S. PATENT DOCUMENTS 10,684,206 B2 * 6/2020 Correia De Matos Nolasco Lamas ............... G01N 15/1436
2007/0269897 A1 * 11/2007 Tanaka ................ G01N 33/493 436/63

(Continued)

FOREIGN PATENT DOCUMENTS

EP 0556971 A2 8/1993
JP H06-288895 A 10/1994
(Continued)

OTHER PUBLICATIONS

Extended European search report issued by the European Patent Office dated May 11, 2021, which corresponds to European Patent Application No. 20215033.0-1001 and is related to U.S. Appl. No. 17/123,792.

(Continued)

*Primary Examiner* — Khai M Nguyen
(74) *Attorney, Agent, or Firm* — Studebaker & Brackett PC

(57) ABSTRACT

A measurement device includes an acquisition unit and a calculation unit. The acquisition unit acquires a first image obtained by image-capturing liquid containing tangible components flowing through a flow path and a second image image-captured simultaneously with the first image and having an image-capturing magnification higher than the first image. The calculation unit sorts, by using clipped images obtained by clipping the tangible components included in the first image and the second image, the tangible components into different types, and that calculates, by using a total number of the tangible components clipped out of the first image and included in a specified category as well as a ratio of a number of each of the tangible components of the different types clipped out of the second image and included in the specified category relative to a total (Continued)

number thereof, the number of the tangible components included in the specified category.

7 Claims, 20 Drawing Sheets

(51) Int. Cl.
*G01N 33/493* (2006.01)
*G06V 10/20* (2022.01)
*G06V 20/69* (2022.01)
*G01N 15/00* (2006.01)

(52) U.S. Cl.
CPC .......... *G06V 20/693* (2022.01); *G06V 20/695* (2022.01); *G06V 20/698* (2022.01); *G01N 2015/0065* (2013.01); *G01N 2015/0693* (2013.01)

(58) Field of Classification Search
CPC .. G06V 20/695; G06V 20/698; G06V 20/693; G06V 20/69; G06V 10/20
See application file for complete search history.

(56) References Cited

U.S. PATENT DOCUMENTS

| | | | |
|---|---|---|---|
| 2008/0019584 A1* | 1/2008 | Lindberg | G06V 20/693 382/134 |
| 2016/0051348 A1* | 2/2016 | Boerjes | A61B 1/24 433/215 |
| 2017/0315039 A1 | 11/2017 | Beil et al. | |
| 2019/0101742 A1* | 4/2019 | Nakajima | G01N 33/493 |
| 2020/0191775 A1* | 6/2020 | So | G01N 33/5094 |

FOREIGN PATENT DOCUMENTS

| | | | | |
|---|---|---|---|---|
| JP | H11-94727 A | | 4/1999 | |
| JP | 2009-544035 A | | 12/2009 | |
| JP | 2020071037 A | * | 5/2020 | ............. G01N 21/05 |

OTHER PUBLICATIONS

An Office Action; "Notice of Reasons for Refusal," mailed by the Japanese Patent Office on Feb. 6, 2024, which corresponds to Japanese Patent Application No. 2020-205362 and is related to U.S. Appl. No. 17/123,792; with English language translation.

* cited by examiner

FIG. 8

| LARGE CATEGORIES | CATEGORY ITEMS | NUMBER |
|---|---|---|
| 1 | RED BLOOD CELL | 30 |
| 2 | WHITE BLOOD CELL | 5 |
| 3 | FLAT EPITHELIUM | 12 |
| | OTHER EPITHELIA | 1 |
| 4 | HYALINE CAST | 0 |
| | OTHER CASTS | 0 |
| 5 | BACTERIA | 30 |
| 6 | CRYSTAL | 2 |
| 7 | OTHERS | 0 |
| 8 | DUST/CELL FRAGMENT | 2 |
| TOTAL NUMBER | - | 82 |

FIG. 9

| LARGE CATEGORIES | CATEGORY ITEMS | NUMBER | RATIO (%) |
|---|---|---|---|
| 1 | RED BLOOD CELL | 10 | 15.2 |
| 2 | WHITE BLOOD CELL | 5 | 7.6 |
| 3 | FLAT EPITHELIUM | 8 | 12.1 |
| | OTHER EPITHELIA | 2 | 3.0 |
| 4 | HYALINE CAST | 0 | 0 |
| | OTHER CASTS | 0 | 0 |
| 5 | BACTERIA | 15 | 22.7 |
| 6 | CRYSTAL | 1 | 1.5 |
| 7 | OTHERS | 2 | 3.0 |
| 8 | DUST/CELL FRAGMENT | 23 | 34.8 |
| TOTAL NUMBER | - | 66 | - |

FIG. 10

| LARGE CATEGORIES | CATEGORY ITEMS | NUMBER |
|---|---|---|
| 1 | RED BLOOD CELL | 12 |
| 2 | WHITE BLOOD CELL | 6 |
| 3 | FLAT EPITHELIUM | 10 |
| | OTHER EPITHELIA | 2 |
| 4 | HYALINE CAST | 0 |
| | OTHER CASTS | 0 |
| 5 | BACTERIA | 19 |
| 6 | CRYSTAL | 1 |
| 7 | OTHERS | 3 |
| 8 | DUST/CELL FRAGMENT | 29 |
| TOTAL NUMBER | - | 82 |

FIG. 13

| LARGE CATEGORIES | CATEGORY ITEMS | NUMBER |
|---|---|---|
| 1 | RED BLOOD CELL | 30 |
| 2 | WHITE BLOOD CELL | 5 |
| 3 | FLAT EPITHELIUM | 10 |
| | OTHER EPITHELIA | 3 |
| 4 | HYALINE CAST | 0 |
| | OTHER CASTS | 0 |
| 5 | BACTERIA | 30 |
| 6 | CRYSTAL | 2 |
| 7 | OTHERS | 0 |
| 8 | DUST/CELL FRAGMENT | 2 |
| TOTAL NUMBER | - | 82 |

FIG. 18

| LARGE CATEGORIES | CATEGORY ITEMS | NUMBER |
|---|---|---|
| 1 | RED BLOOD CELL | 30 |
| 2 | WHITE BLOOD CELL | 5 |
| 3 | EPITHELIUM | 16 |
| 4 | CAST | 5 |
| 5 | BACTERIA | 30 |
| 6 | CRYSTAL | 10 |
| 7 | OTHERS | 0 |
| 8 | DUST/CELL FRAGMENT | 5 |
| TOTAL NUMBER | - | 101 |

FIG. 19

| LARGE CATEGORIES | CATEGORY ITEMS | NUMBER | RATIO (%) |
|---|---|---|---|
| 1 | ISOMORPHIC RED BLOOD CELL | 8 | 10.0 |
| | DYSMORPHIC RED BLOOD CELL | 7 | 8.8 |
| 2 | NEUTROPHIL | 5 | 6.3 |
| | LYMPHOCYTE/ACIDOPHIL/MONOCYTE | 0 | 0 |
| 3 | FLAT EPITHELIUM | 2 | 2.5 |
| | TUBULAR EPITHELIUM | 4 | 5.0 |
| | UROTHELIUM | 8 | 10.0 |
| | AMEBOCYTE | 0 | 0 |
| 4 | HYALINE CAST | 2 | 2.5 |
| | GRANULAR CAST | 0 | 0 |
| | EPITHELIAL CAST | 5 | 6.3 |
| | OTHER CASTS | 0 | 0 |
| 5 | BACILLUS | 10 | 12.5 |
| | COCCUS | 5 | 6.3 |
| 6 | SALTS/NORMAL CRYSTAL | 4 | 5.0 |
| | ABNORMAL CRYSTAL | 0 | 0 |
| 7 | OTHERS | 5 | 6.3 |
| 8 | DUST/CELL FRAGMENT | 15 | 18.8 |
| TOTAL NUMBER | - | 80 | - |

FIG. 20

| LARGE CATEGORIES | CATEGORY ITEMS | NUMBER |
|---|---|---|
| 1 | ISOMORPHIC RED BLOOD CELL | 10 |
| | DYSMORPHIC RED BLOOD CELL | 9 |
| 2 | NEUTROPHIL | 6 |
| | LYMPHOCYTE/ACIDOPHIL/MONOCYTE | 0 |
| 3 | FLAT EPITHELIUM | 3 |
| | TUBULAR EPITHELIUM | 5 |
| | UROTHELIUM | 10 |
| | AMEBOCYTE | 0 |
| 4 | HYALINE CAST | 3 |
| | GRANULAR CAST | 0 |
| | EPITHELIAL CAST | 6 |
| | OTHER CASTS | 0 |
| 5 | BACILLUS | 13 |
| | COCCUS | 6 |
| 6 | SALTS/NORMAL CRYSTAL | 5 |
| | ABNORMAL CRYSTAL | 0 |
| 7 | OTHERS | 6 |
| 8 | DUST/CELL FRAGMENT | 19 |
| TOTAL NUMBER | - | 101 |

MEASUREMENT DEVICE AND MEASUREMENT METHOD

CROSS-REFERENCE

This application claims priority to Japanese Patent Application No. 2019-227645, filed on Dec. 17, 2019, and Japanese Patent Application No. 2020-205362, filed on Dec. 10, 2020, the entire contents of which are incorporated herein by reference.

FIELD

The present disclosure relates to a measurement device and a measurement method.

BACKGROUND

As one type of urine test methods, a method is known which image-captures a urine specimen flowing through a flow path provided in a flow cell and analyzes an captured image to sort sediments (tangible (solid) components in the urine such as blood cells, epithelial cells, casts, bacteria, and crystals) in urine into different types of components (see, e.g., Patent Document 1 and Patent Document 2).

DOCUMENT OF RELATED ART

Patent Document

[Patent Document 1] Japanese Laid-Open Patent Publication No. H06-288895
[Patent Document 2] Japanese Laid-Open Patent Publication No. H11-94727

SUMMARY

An aspect of a technique according to the disclosure is shown by way of example by a measurement device as described below. A measurement device includes an acquisition unit and a calculation unit. The acquisition unit acquires a first image obtained by image-capturing liquid containing tangible components flowing through a flow path and a second image image-captured simultaneously with the first image and having an image-capturing magnification higher than that of the first image. The calculation unit sorts, by using clipped images obtained by clipping the tangible components included in the first image and the second image, the tangible components into different types, and that calculates, by using a total number of the tangible components clipped out of the first image and included in a specified category as well as a ratio of a number of each of the tangible components of the different types clipped out of the second image and included in the specified category relative to a total number of the tangible components in the specified category, the number of the tangible components included in the specified category.

The technique according to the disclosure sorts the tangible components contained in the liquid and can increase the accuracy of calculating the numbers of the sorted tangible components.

BRIEF DESCRIPTION OF THE DRAWINGS

FIG. 8 is a diagram illustrating an example of results of the sorting of the tangible components and the calculation of the number of the tangible components each based on a first image;

FIG. 9 is a diagram illustrating an example of results of the sorting of the tangible components and calculation of ratios of the numbers of the tangible components each based on a second image;

FIG. 10 is a diagram illustrating a correction result obtained by performing correction processing in the embodiment;

FIG. 13 is a diagram illustrating an example of the correction result obtained by performing the correction processing in the first modification;

FIG. 18 is a diagram illustrating an example of the results of the sorting of the tangible components and the calculation of the number of the tangible components each based on the first image in the third modification;

FIG. 19 is a diagram illustrating an example of the results of the sorting of the tangible components and the calculation of the ratios of the numbers of the tangible components each based on the second image in the third modification; and FIG. 20 is a diagram illustrating the correction result obtained by performing the correction processing in the third modification.

DESCRIPTION OF EMBODIMENTS

Figure 1:
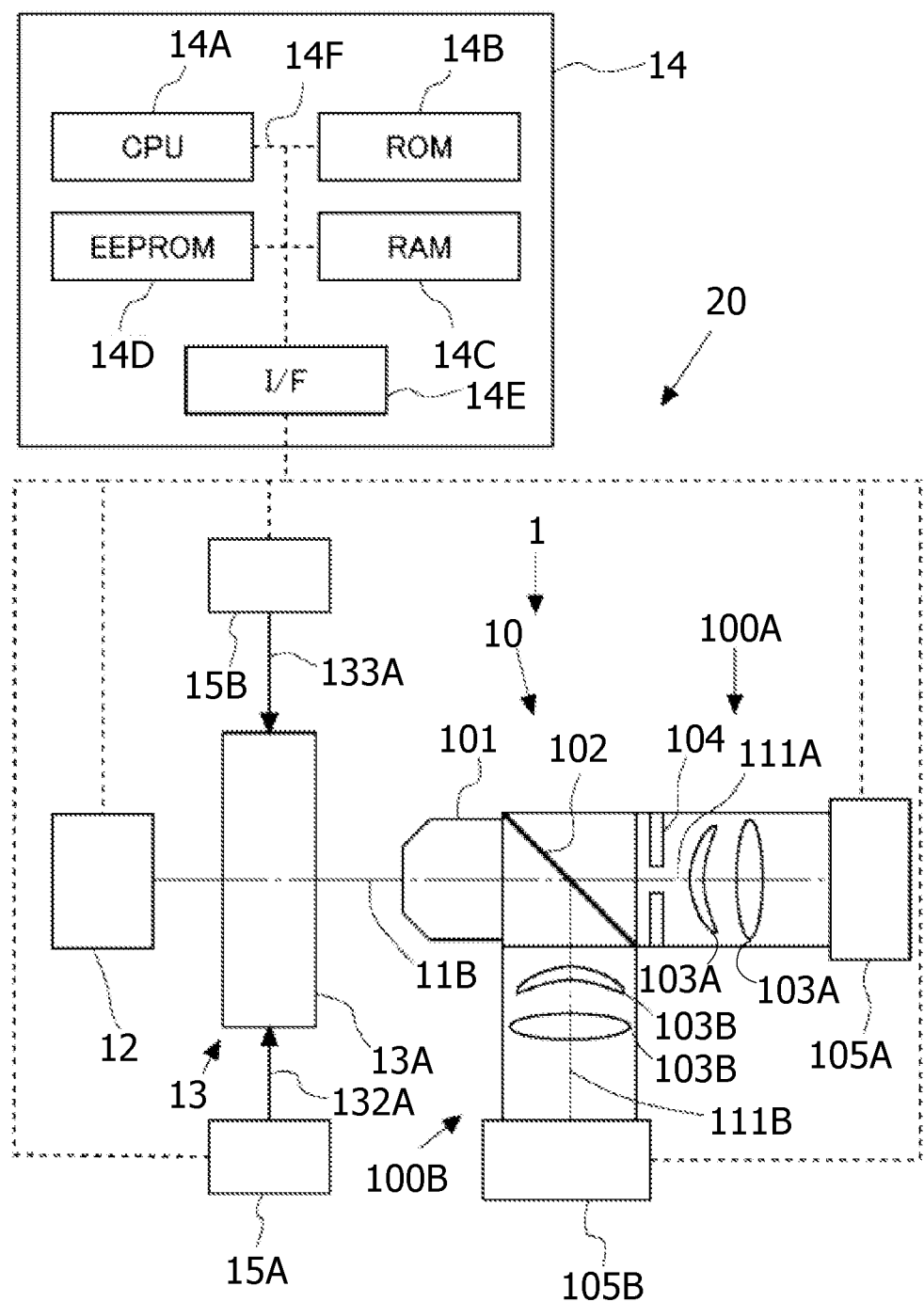
FIG. 1 is a diagram illustrating a schematic configuration of a measurement device according to an embodiment.

The analysis of the sediments in the urine includes determination processing of determining types of the sediments in the urine and calculation processing of calculating the number of the sediments. By image-capturing the urine specimen with a high magnification, it is possible to recognize in detail shapes of the sediments and therefore increase accuracy of the determination processing. Meanwhile, when the urine specimen is image-captured with a high magnification, an image-capturing range is narrowed, thereby increasing the number of the sediments passing through a range outside the image-capturing range and degrading a capture rate in a captured image.

When the image-capturing range is widened to reduce the number of the sediments passing through the range outside the image-capturing range in order to increase accuracy of the calculation processing, the urine specimen is consequently image-captured with a low magnification. When the urine specimen is image-captured with the low magnification, the detailed shapes and structures of the sediments can no longer be recognized to result in degraded accuracy of the determination processing. Such a problem is not limited to the image-capturing of the urine specimen, and may arise also when tangible components contained in liquid other than urine, such as blood, a bodily fluid, or artificial blood, are determined, and the number of the tangible components is counted. In Japanese Laid-Open Patent Publication No. H 06-288895, scattered light scattered by particles flowing in a flow cell is detected using a detector, and an image is captured in accordance with a detection signal. In Japanese Laid-Open Patent Publication No. H 11-94727, before sample measurement, an image effective factor is acquired using a known standard sample, the number of image processing particles is calculated from the number of all the particles passing through an image-capturing region of the flow cell, and the number of the image processing particles is multiplied by the particles image effective factor, whereby the number of the particles is calculated. However, in the particle detection using the scattered light, the particles cannot be sorted on a per component basis. As a result, there has been a demand for a further improvement in measurement accuracy.

A task of the disclosure is to increase accuracy of measurement in which tangible components contained in liquid are sorted and the number of each of the sorted tangible components is calculated.

Embodiments

A further description will be given below of an embodiment. A configuration of the embodiment shown below is exemplary, and a technique according to the disclosure is not limited to the configuration of the embodiment. For example, a measurement device according to the embodiment includes the following configuration. The measurement device according to the embodiment includes an acquisition unit and a calculation unit. The acquisition unit acquires a first image obtained by image-capturing liquid containing tangible components flowing through a flow path and a second image image-captured simultaneously with the first image and having an image-capturing magnification higher than that of the first image. The calculation unit sorts, by using clipped images obtained by clipping the tangible components included in the first image and the second image, the tangible components into different types, and that calculates, by using a total number of the tangible components clipped out of the first image and included in a specified category as well as a ratio of a number of each of the tangible components of the different types clipped out of the second image and included in the specified category relative to a total number of the tangible components in the specified category, the number of the tangible components included in the specified category.

The measurement device determines the types of the tangible components contained in the liquid and calculates the numbers of the tangible components of the different types. In the measurement device, the liquid may be liquid derived from a living body such as, e.g., urine, blood, or a bodily fluid or may also be liquid not derived from a living body such as artificial blood or a chemical. When the specimen is urine, as the tangible components, blood cells, epithelial cells, casts, bacteria, crystals, and the like can be listed.

Preferably, the flow path is formed such that the tangible components contained in the liquid do not stay in one place, but are uniformly distributed in the liquid to flow. The tangible components thinly spread in the liquid to inhibit degradation of accuracy of calculating the numbers of the tangible components due to the plurality of overlapping tangible components observed in the first image or the second image. For example, the flow path is formed in the flow cell.

The acquisition unit acquires the first image and the second image. The acquisition unit may also acquire the first image and the second image from an image capturing unit that has captured the first image and the second image. Alternatively, the acquisition unit may also acquire, from a storage unit, the first image and the second image each stored in advance in the storage unit. Still alternatively, the acquisition unit may also receive the first image and the second image from another device via a communication line or the like.

For example, the image capturing unit is a digital camera including an image capturing element such as a charge coupled device (CCD) image sensor or a complementary metal oxide semiconductor (CMOS) image sensor.

The first image is lower in magnification than the second image, and accordingly a wider range is captured in the first image. Consequently, the number of the tangible components captured by the captured first image is large, and therefore the first image is appropriate for counting of the number of the tangible components. Meanwhile, the second image captured with a magnification higher than that with which the first image is captured can show detailed shapes and structures of the tangible components. Accordingly, the second image is appropriate for sorting of the tangible components. The measurement device calculates the number of at least one type of the tangible components by using the number of the tangible components included in the first image and the numbers of the tangible components of the different types included in the second image to be able to increase the accuracy of calculating the numbers of the tangible components.

The measurement device may also have the following characteristic feature. The calculation unit mentioned above multiplies the total number of the tangible components clipped out of the first image described above and included in a specified category by a ratio of the number of each of the tangible components of the different types clipped out of the second image and included in the specified category relative to a total number of the tangible components in the specified category, thereby calculating the number of the tangible components included in the specified category. The specified category (type) mentioned herein may be, e.g., all the categories, the category (type) specified by a person in charge of the measurement, or the category (type) prone to erroneous sorting. By having such a characteristic feature, it is possible to increase the accuracy of calculating the number of the tangible components in the specified category (of the specified type), while reducing an arithmetic load placed on the measurement device.

The measurement device may also have the following characteristic feature. The calculation unit outputs a complete component image in which clipped images representing the tangible components of the different types are disposed based on a result of calculating the numbers of the tangible components of the different types. By having such a characteristic feature, the measurement device can facilitate visual recognition of the types of the tangible components and the number of the tangible components.

The measurement device may also have the following characteristic feature. The measurement device further includes a first image capturing unit that image-captures the first image and a second image capturing unit that image-captures the second image, and the first image capturing unit and the second image capturing unit have the same focal positions on optical axes thereof. By having such a characteristic feature, it is possible to increase the accuracy of calculating the number of the tangible components, since the image-capturing range of the second image is included in the image-capturing range of the first image in an in-focus state. The technique according to the embodiment described above can also be recognized from the aspect of a measurement method.

Referring to the drawings, a further description will be given below of the measurement device according to the embodiment. FIG. 1 is a diagram illustrating a schematic configuration of the measurement device according to the embodiment. A measurement device 20 includes an image-capturing device 1. The measurement device 20 uses the image-capturing device 1 to imager-capture, e.g., urine as a specimen and analyzes a captured image to measure, e.g., tangible components in the urine. However, the measurement device 20 is also applicable to measurement of tangible components in liquid specimen other than urine such as, e.g., blood or a bodily fluid. The urine is an example of a "liquid containing tangible components".

The image-capturing device 1 includes an image capturing unit 10 that image-captures the specimen, a light source 12 for the image-capturing, and a flow cell unit 13. The flow cell unit 13 includes a stage (the illustration thereof is omitted) on which a flow cell 13A through which the specimen flows is fixedly disposed. The flow cell 13A is detachable from the stage.

The image capturing unit 10 includes an objective lens 101, a branching portion 102, a first lens set 103A, a second lens set 103B, an aperture 104, a first camera 105A, and a second camera 105B. Each of the first camera 105A and the second camera 105B uses an image capturing element such as, e.g., a CCD image sensor or a CMOS image sensor to perform the image-capturing. A combination of the objective lens 101, the branching portion 102, the first lens set 103A, the aperture 104, and the first camera 105A is hereinafter referred to as a first image capturing unit 100A. Meanwhile, a combination of the objective lens 101, the branching portion 102, the second lens set 103B, and the second camera 105B is referred to as a second image capturing unit 100B. Each of the first lens set 103A and the second lens set 103B includes an ocular lens and may also have an imaging lens. The flow cell 13A is disposed between the light source 12 and the objective lens 101. The light source 12 and the objective lens 101 are shared by the first image capturing unit 100A and the second image capturing unit 100B. The objective lens 101 may be of either a finite-corrected optical system or an infinity-corrected optical system but, by using the objective lens 101 of the finite-corrected optical system, it is possible to compactify the image-capturing device 1. The first image capturing unit 100A is an example of a "first image capturing unit". The second image capturing unit 100B is an example of a "second image capturing unit".

For example, the branching portion 102 is a beam splitter such as a half mirror. The branching portion 102 allows a portion of light that has passed through the flow cell 13A and the objective lens 101 to pass therethrough and reflects a remaining portion of the light to branch the light in two directions. Light resulting from the branching and transmitted by the branching portion 102 is incident on an image-capturing surface of an image capturing element of the first camera 105A through the first lens set 103A. In other words, the light transmitted by the branching portion 102 is subjected to image-capturing in the first image capturing unit 100A. Meanwhile, the light reflected by the branching portion 102 is incident on an image capturing surface of an image capturing element of the second camera 105B through the second lens set 103B. In other words, the light reflected by the branching portion 102 is subjected to image-capturing in the second image capturing unit 100B. An optical path for the light between the branching portion 102 and the first camera 105A is referred to as a first optical path, while an optical path for the light between the branching portion 102 and the second camera 105B is referred to as a second optical path. As illustrated in FIG. 1, the branching portion 102 is disposed on an optical axis 11B of the objective lens 101. In FIG. 1, an optical axis of the first optical path is denoted by 111A, while an optical axis of the second optical path is denoted by 111B.

The aperture 104 is disposed between the branching portion 102 and the first lens set 103A. In other words, the aperture 104 is inserted in the first optical path. The aperture 104 is formed by opening a circular hole in a plate. The aperture 104 is disposed at a position to be perpendicular to the optical axis 111A of the first optical path such that an optical axis 111A of the first lens set 103A passes through a center axis of the hole of the aperture 104. The aperture 104 is a diaphragm which blocks, in the first optical path, light from a peripheral portion to reduce an optical aperture of light traveling toward the first camera 105A. The aperture 104 increases a depth of field of the first camera 105A.

In the measurement device 20, a controller 14 is provided to serve as a control unit. The controller 14 includes a central processing unit (CPU) 14A, a read only memory (ROM) 14B, a random access memory (RAM) 14C, an electrically erasable programmable read only memory (EEPROM) 14D, and an interface circuit 14E. The CPU 14A, the ROM 14B, the RAM 14C, the EEPROM 14D, and the interface circuit 14E are connected to each other by a bus line 14F.

The CPU 14A controls the entire measurement device 20 based on a program stored in the ROM 14B and read into the RAM 14C. In the ROM 14B, programs and data for operating the CPU 14A are stored. The RAM 14C provides a work area for the CPU 14A and temporarily stores various data and programs. The EEPROM 14D stores various setting data and the like. The interface circuit 14E controls communication between the CPU 14A and the various circuits.

To the interface circuit 14E, control lines for the first image capturing unit 100A, the second image capturing unit 100B, the light source 12, a first pump 15A, and a second pump 15B are connected. The first image capturing unit 100A, the second image capturing unit 100B, the light source 12, the first pump 15A, and the second pump 15B are controlled by a control signal from the CPU 14A. The first pump 15A is a pump that supplies a sheath fluid to the flow cell 13A via a first supply pipe 132A. The second pump 15B is a pump that supplies the specimen to the flow cell 13A via a second supply pipe 133A. The sheath fluid is liquid that controls a flow of the specimen in the flow cell 13A. As an example of the sheath fluid when the specimen is, e.g., urine, normal saline can be used. However, a solution other than the normal saline may also be used as the sheath fluid.

Figure 2:
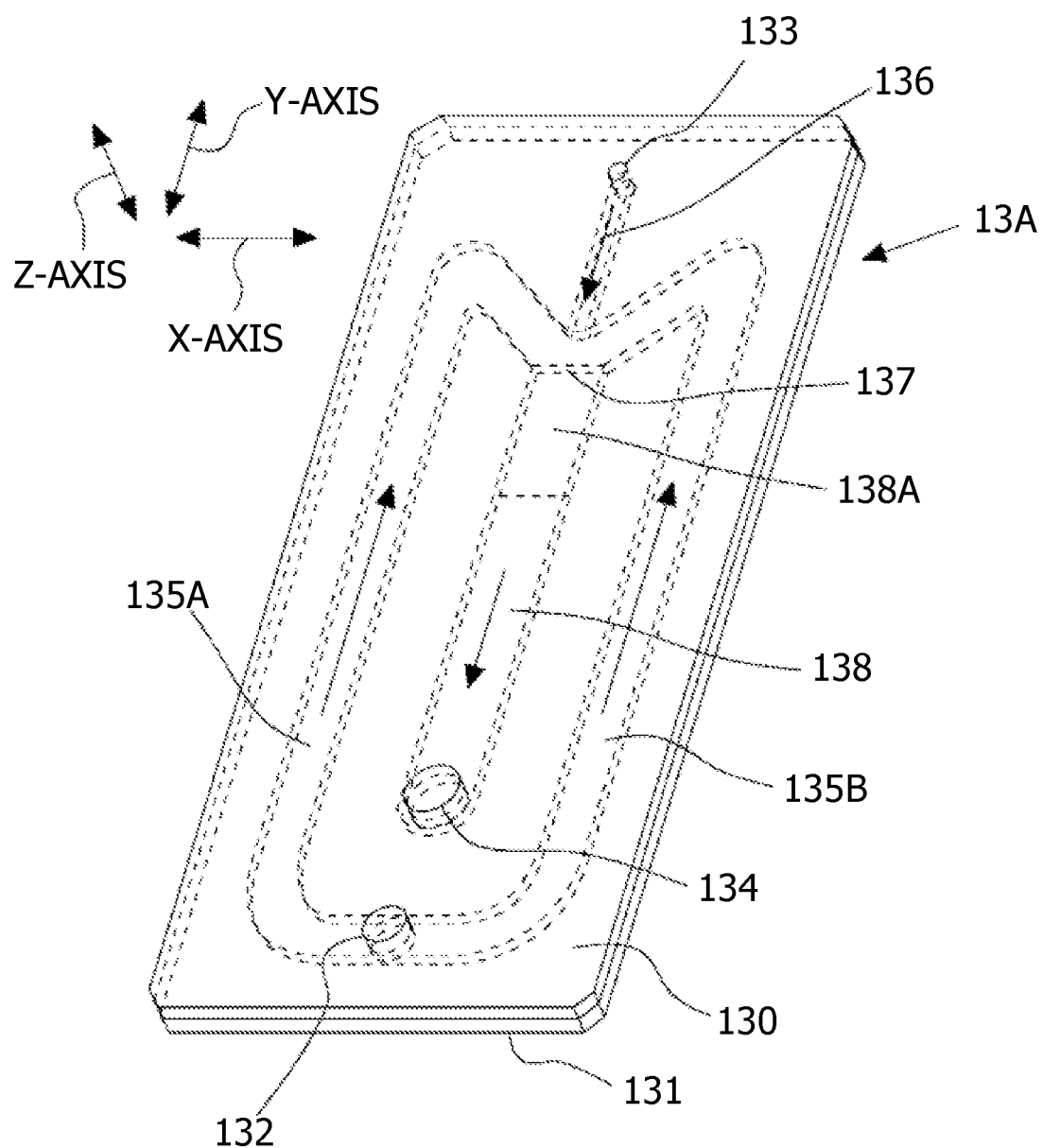
FIG. 2 is a diagram illustrating a schematic configuration of a flow cell.

FIG. 2 is a diagram illustrating a schematic configuration of the flow cell 13A. The flow cell 13A is formed by joining together a first plate 130 and a second plate 131 (by, e.g., thermocompression). FIG. 2 is a diagram obtained by viewing the flow cell 13A from the first plate 130 side. It is assumed that a width direction of the flow cell 13A illustrated in FIG. 2 is an X-axis direction in a rectangular coordinate system, a longitudinal direction of the flow cell 13A is a Y-axis direction in the rectangular coordinate system, and a thickness direction of the flow cell 13A is a Z-axis direction in the rectangular coordinate system. The specimen to be image-captured flows in the Y-axis direction in the flow cell 13A. The optical axis 11B of the objective lens 101 is disposed to extend in the Z-axis direction.

As a material of the flow cell 13A, a material having a visible light transmissivity of, e.g., 90% or more, such as acrylic resin (PMMA), cycloolefin polymer (COP), polydimethylsiloxane (PDMS), polypropylene (PP), or quartz glass, can be used.

In the first plate 130, a first supply hole 132 for supplying the sheath fluid, a second supply hole 133 for supplying the specimen, and an exhaust hole 134 for exhausting the sheath fluid and the specimen are provided. Each of the first supply hole 132, the second supply hole 133, and the exhaust hole 134 extends through the first plate 130 in a thickness direction thereof. The first supply hole 132 is provided closer to one end of the first plate 130 in a longitudinal direction thereof. The second supply hole 133 is provided closer to the other end of the first plate 130 in the longitudinal direction thereof. The exhaust hole 134 is provided between the first supply hole 132 and the second supply hole 133 in the first plate 130 in the longitudinal direction thereof.

The first supply hole 132, the second supply hole 133, and the exhaust hole 134 communicate with each other via paths 135A, 135B, 136, and 138. Each of the paths 135A, 135B, 136, and 138 is formed of a junction-plane surface of the first plate 130 which is recessed to have a rectangular cross section. Each of the paths 135A, 135B, 136, and 138 is also formed to have the cross section which is longer in a width direction thereof (the X-axis direction in FIG. 2) than in a depth direction thereof (the Z-axis direction in FIG. 2). When the first plate 130 and the second plate 131 are joined together, the second plate 131 serves as a wall material in which the paths 135A, 135B, 136, and 138 are to be formed.

To the first supply hole 132, the first path 135A and the second path 135B are connected. The first path 135A and the second path 135B extend in opposite directions along an outer edge of the first plate 130 toward the second supply hole 133 to be joined together in a confluent portion 137. To the second supply hole 133, the third path 136 is connected. The third path 136 is joined with the first path 135A and the second path 135B in the confluent portion 137. The confluent portion 137 is connected to the exhaust hole 134 via the fourth path 138. In the fourth path 138, a tapered portion 138A is formed in a tapered shape in which a depth of the fourth path 138 (a length of the first plate 130 in the plate thickness direction (the Z-axis direction)) gradually decreases with distance from the confluent portion 137 toward the exhaust hole 134. The tapered portion 138A is provided with an inclination of, e.g., 2° to 8°.

To the first supply hole 132, the first supply pipe 132A illustrated in FIG. 1 is connected. To the second supply hole 133, the second supply pipe 133A illustrated in FIG. 1 is connected. To the exhaust hole 134, an exhaust pipe (the illustration thereof is omitted) is connected. The sheath fluid supplied from the first supply pipe 132A to the first supply hole 132 flows through the first path 135A and the second path 135B. The specimen supplied from the second supply pipe 133A to the second supply hole 133 flows through the third path 136. The sheath fluid and the specimen join together in the confluent portion 137 to flow through the fourth path 138 to be exhausted from the exhaust hole 134 into the exhaust pipe.

Figure 3:
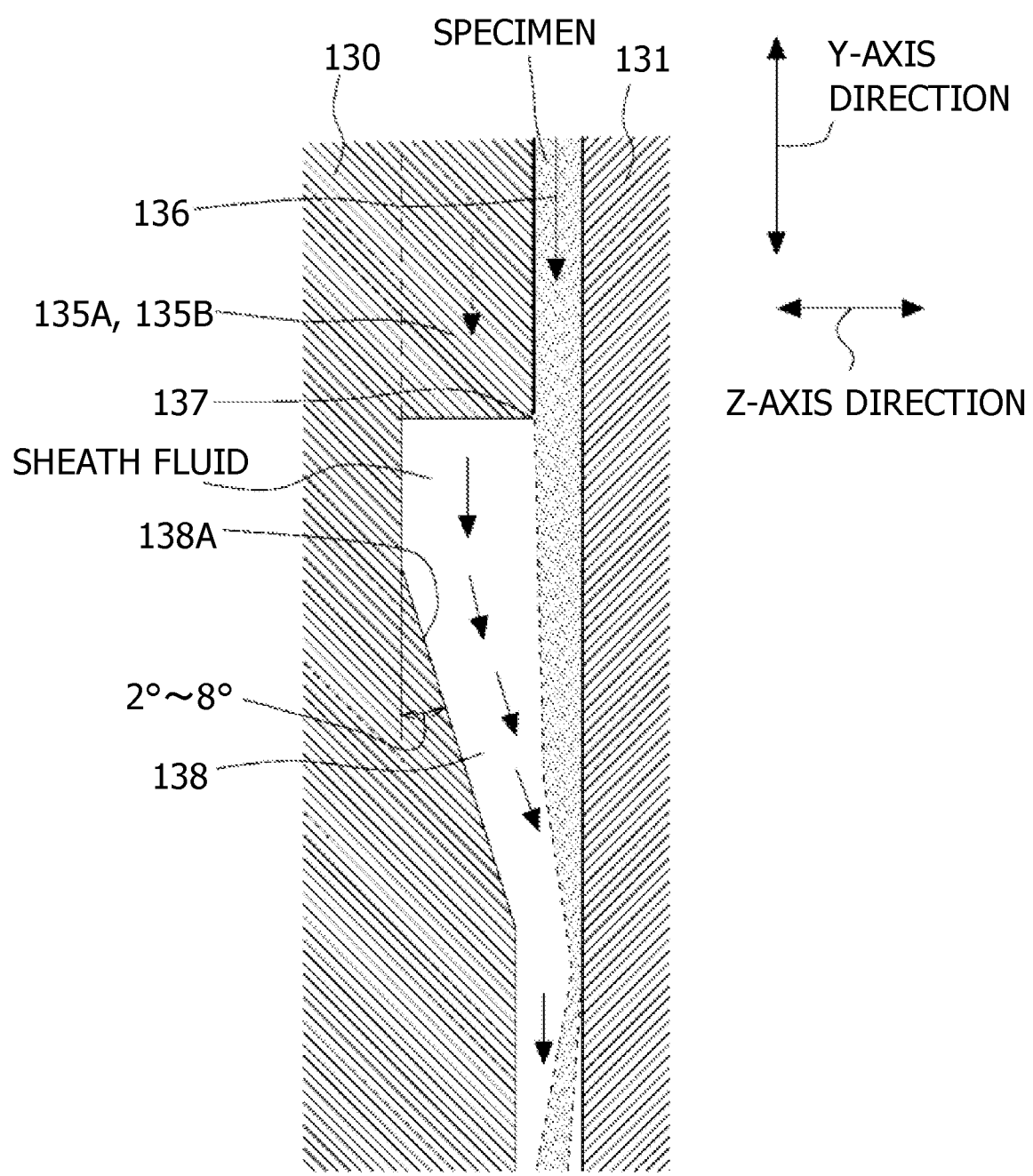
FIG. 3 is a diagram illustrating a schematic configuration of the vicinity of each of a confluent portion and a tapered portion.

FIG. 3 is a diagram illustrating a schematic configuration of the vicinity of each of the confluent portion 137 and the tapered portion 138A. In the confluent portion 137, the third path 136 is unevenly disposed to be closer to the second plate 131. In the confluent portion 137, the specimen flows along the second plate 131.

Figure 4:
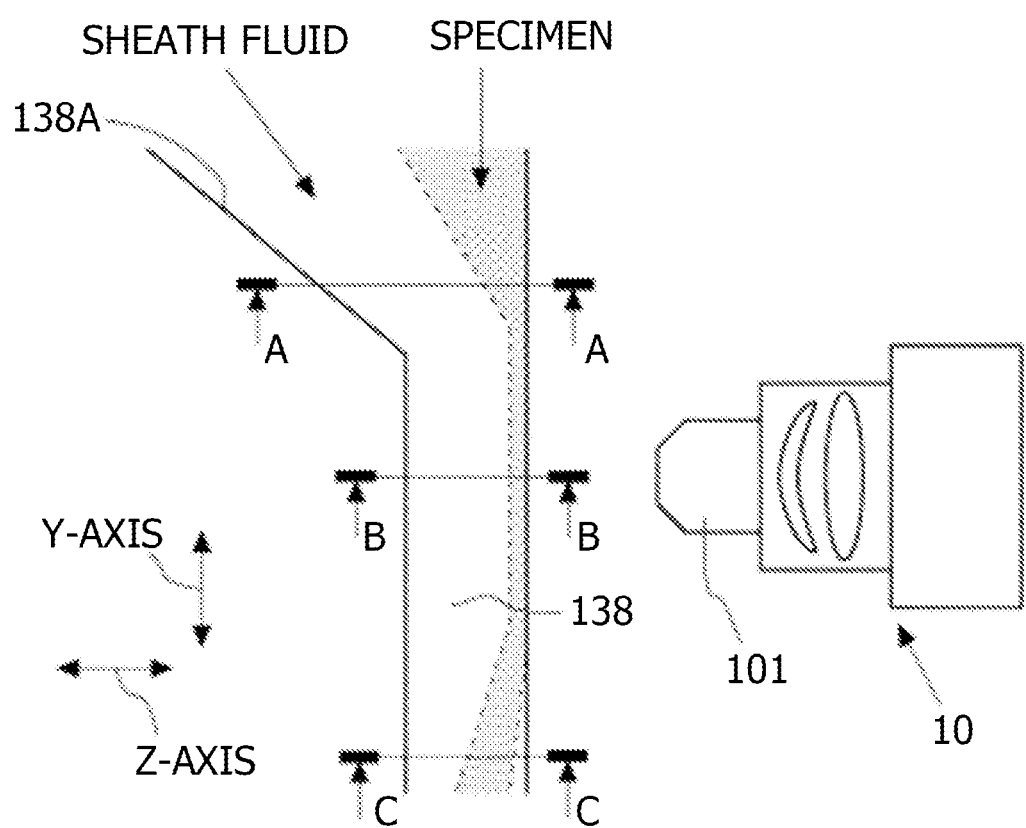
FIG. 4 is a diagram illustrating distributions of a sheath fluid and a specimen each flowing through a fourth path.

FIG. 4 is a diagram illustrating distributions of the sheath fluid and the specimen each flowing through the fourth path 138. After the sheath fluid and the specimen are separately supplied from an upper side in FIG. 4, the sheath fluid and the specimen join together in the confluent portion 137. Immediately after the joining together of the sheath fluid and the specimen in the confluent portion 137, the specimen in the sheath fluid is localized to a relatively narrow range closer to a wall surface of the second plate 131 (position along a line A-A). Then, when the specimen flows through the tapered portion 138A, the specimen is pressed by the sheath fluid to spread into a flat shape along and near the wall surface of the second plate 131 (position along a line B-B). When the specimen further flows, the specimen moves away from the wall surface of the second plate 131 under a tubular-pinch effect to be raised to a center direction of the fourth path 138 (position along a line C-C).

A distribution of the tangible components is affected by a distribution of the specimen in the sheath fluid. The measurement device 20 performs image-capturing using the first image capturing unit 100A and the second image capturing unit 100B at a position at which a larger number of the tangible components can be image-captured to be able to increase the accuracy of measuring the tangible components. In the flow cell 13A, a flow of the specimen varies depending on a position thereof in the Y-axis direction. At the position along the line C-C in FIG. 4, a width of the specimen in the Z-axis direction is larger than at the position along the line B-B. At the position along the line C-C in FIG. 4, the tangible components in the specimen are distributed to spread in the Z-axis direction, and therefore the position along the line C-C is inappropriate for the image-capturing of the tangible components.

Meanwhile, at the position along the line B-B in FIG. 4, the sheath fluid flows from above so as to press the specimen against the second plate 131, and the specimen is crushed under the pressure of the sheath fluid to thinly spread in the optical axis direction. Consequently, at the position along the line B-B in FIG. 4, the tangible components in the specimen are present without spreading in the Z-axis direction. Note that the sheath fluid and the specimen form respective laminar flows and are scarcely mixed with each other. Such a position along the line B-B is a position in the Y-axis direction appropriate for the image-capturing of the tangible components, and therefore the measurement device 20 image-captures the specimen at this position in the Y-axis direction. This position is referred to as an image-capturing position, and the optical axis 11B of the objective lens 101 is aligned with the image-capturing position. In other words, the flow cell 13A is formed such that the tangible components thinly spread in the specimen at the image-capturing position. At the image-capturing position, the tangible components are uniformly distributed in the specimen.

Note that the description has been given by way of example of a mode in which the specimen after passing through the tapered portion 138A of the flow cell 13A is in contact with a wall surface of the flow cell 13A. However, a structure of the flow cell and the flow of the specimen are not limited to those in this mode. In the measurement device 20, e.g., a flow cell having a structure in which, after the passage of the specimen through the tapered portion 138A of the flow cell 13A, the sheath fluid surrounds the specimen, and the specimen is thinly stretched out in a center portion of the sheath fluid may also be used.

Returning back to FIG. 1, in the first image capturing unit 100A, the aperture 104 is inserted in the first optical path to reduce an amount of the light travelling toward the first camera 105A (reduce a numerical aperture). Meanwhile, in the second optical path, a diaphragm equivalent to the aperture 104 is not provided. In the first camera 105A, the numerical aperture of the aperture 104, respective magnifications of individual lenses included in the first lens set 103A, a distance between the objective lens 101 and the first lens set 103A, and the like are adjusted to set an image-capturing magnification at the image-capturing position to a first magnification. In the second camera 105B, respective magnifications of individual lenses included in the second lens set 103B, a distance between the objective lens 101 and the second lens set 103B, and the like are adjusted to set the image-capturing magnification at the image-capturing position to a second magnification higher than the first magnification. For example, the first magnification and the second magnification may also be 10 times and 40 times, respectively. Focal positions of the first camera 105A and the second camera 105B on the respective optical axes thereof are adjusted to coincide with the same position in the specimen in the image-capturing at the image-capturing position. In other words, the first camera 105A and the second camera 105B have the same focal positions.

The CPU 14A causes the first camera 105A and the second camera 105B to simultaneously capture still images of the tangible components in the specimen flowing through the flow cell 13A. The still images are enlarged images of the specimen. An ON period of the light source 12 and respective image-capturing periods (exposure periods) of the first camera 105A and the second camera 105B are synchronized by the CPU 14A. From the light source 12, parallel beams are incident on the flow cell 13A. In image-capturing the still images, the CPU 14A turns ON the light source 12 once or a plurality of times. The ON period of the light source 12 depends on a flow rate of the specimen and is set to, e.g., 0.1 to 10 psec to allow motion blur to fall within an allowable range. It may also be possible to turn ON the light source 12 a plurality of times for one exposure shot and thus increase the number of the tangible components included in one image. By image-capturing a larger number of the tangible components, the measurement device 20 can further increase the accuracy of measuring the tangible components. In this case, timing of blinking the light source 12 may be determined appropriately in consideration of a relationship between the flow rate of the specimen and the ON period of the light source 12. In measurement for one specimen, e.g., 100 to 1000 images are captured. As the light source 12, e.g., a xenon lamp or a white LED can be used, but the light source 12 is not limited thereto, and another light source can also be used.

Figure 5:
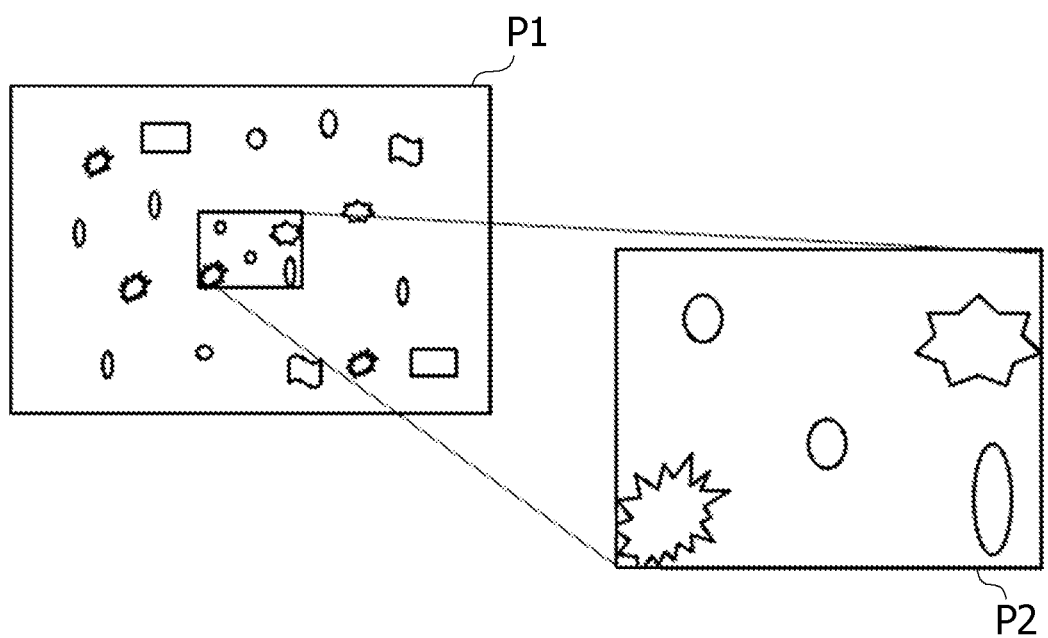
FIG. 5 is a diagram illustrating an example of respective images captured by a first image capturing unit and a second image capturing unit.

When an image of the light from the light source 12 transmitted by the flow cell 13A is image-captured by the first image capturing unit 100A and the second image capturing unit 100B, two images having different image-capturing magnifications are acquired. FIG. 5 is a diagram illustrating an example of the respective images captured by the first image capturing unit 100A and the second image capturing unit 100B. In FIG. 5, a first image P1 is an example of an image captured by the first image capturing unit 100A with the first magnification at the image-capturing position. Meanwhile, a second image P2 is an example of an image captured by the second image capturing unit 100B with the second magnification at the image-capturing position. As illustrated in FIG. 5, the second image P2 corresponds to an image obtained by enlarging a local region of the first image P1. In addition, the first camera 105A and the second camera 105B have the same focal positions on the respective optical axes thereof. The first image P1 and the second image P2 have respective center positions in an XY plane which are coincident with each other, and an image-capturing range of the second image P2 may appropriately be included in an image-capturing range of the first image P1. In other words, an image-captured region image-captured by the second image capturing unit 100B is included in an image-captured region image-captured by the first image capturing unit 100A. The respective image-captured regions image-captured by the two image capturing units are associated with each other. For example, the CPU 14A acquires, from the first image capturing unit 100A and the second image capturing unit 100B, the first image P1 and the second image P2 simultaneously captured thereby and stores the acquired first and second images P1 and P2 in association with each other in the RAM 14C. The first image P1 is an example of a "first image". The second image P2 is an example of a "second image".

The first image P1, which is wider in image-capturing range than the second image P2, is appropriate for determination of the number of the tangible components. Meanwhile, the second image P2, which is higher in image-capturing magnification than the first image P1, is appropriate for observation of shapes of cell nuclei or the like or sorting of the tangible components. For example, the CPU 14A can calculate the number of the tangible components in the specimen based on the first image P1, sort the tangible components in the specimen into different types based on the second image P2, and calculate the number of each of the tangible components sorted into the different types.

The CPU 14A recognizes positions and sizes of the tangible components and the number of the tangible components in the images captured by the first image capturing unit 100A and the second image capturing unit 100B, determines sizes of images to be clipped based on the recognized sizes of the tangible components, and generates clipped images. The clipped images are images obtained by comparing the captured images to a background image, encircling portions with differences, and clipping images in the encircled portions.

Prior to generation of the clipped images, the CPU 14A uses data on the stored images to produce, for each of the images, an average of respective pixel values of individual pixels as the background image. The pixel values may be either luminances or RGB values of the individual pixels. The clipped images are generated through execution of the program (clipping processing) stored in the ROM 14B by the CPU 14A. The clipped images are stored together with positions at which the images are clipped and the sizes of the clipped images in the RAM 14C. For example, the CPU 14A determines that portions of each of the first image P1 and the second image P2 that have differences with the background image include the tangible components and generates the clipped images for all the tangible components included in the image. The CPU 14A sorts the clipped images clipped out of the first image P1 according to each of the tangible components and counts the number of each of the clipped images sorted into different category items. The CPU 14A may also calculate only the total number of the tangible components in the specimen without sorting the clipped images clipped out of the first image P1 according to each of the tangible components. The CPU 14A also observes shapes of the tangible components in each of the clipped images clipped out of the second image P2, sorts the tangible components into the different types, and calculates the numbers of the tangible components sorted into the different types.

Figure 6:
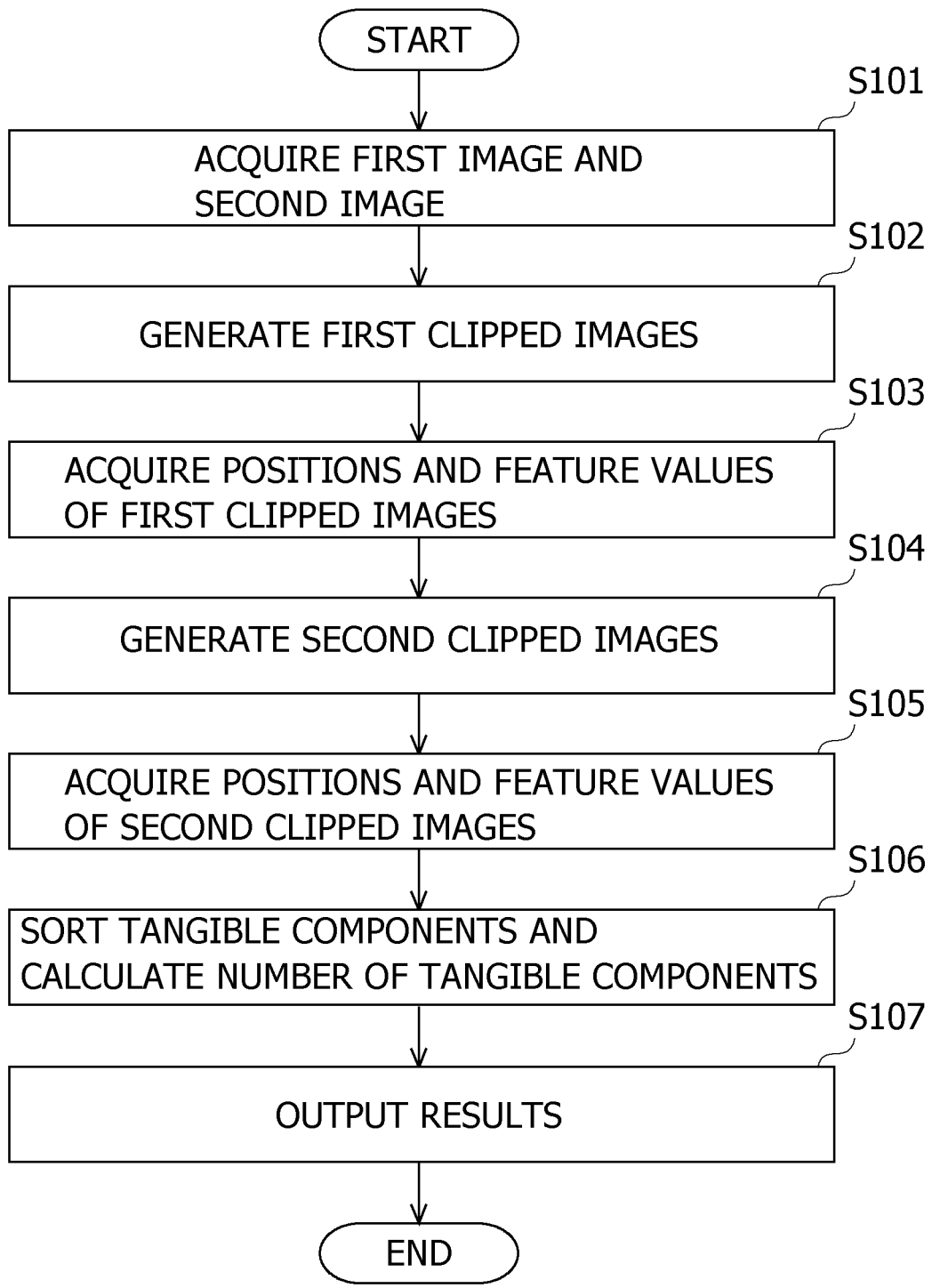
FIG. 6 is a flow chart illustrating a flow of sorting of tangible components in the embodiment.

FIG. 6 is a flow chart illustrating a flow of the sorting of the tangible components in the embodiment. The flow chart illustrated in FIG. 6 is executed by the CPU 14A.

In S101, the CPU 14A acquires the first image P1 captured by the first image capturing unit 100A. The CPU 14A also acquires the second image P2 captured by the second image capturing unit 100B. The CPU 14A stores the first image P1 and the second image P2 in the RAM 14C. The CPU 14A that performs the processing in S101 is an example of the "acquisition unit". The processing in S101 is an example of an "acquisition step".

In S102, the CPU 14A clips the tangible components out of the first image P1 to generate first clipped images. The CPU 14A stores the generated first clipped images in the RAM 14C.

In S103, the CPU 14A acquires positional information and feature values of the first clipped images stored in the RAM 14C in S102. The CPU 14A stores the first clipped images and the positional information and the feature values of the first clipped images in association with each other in the RAM 14C. Examples of the feature values include colors, shapes, and sizes. To acquire the feature values, the program stored in advance in the ROM 14B is used.

In S104, the CPU 14A clips the tangible components out of the second image P2 to generate second clipped images. The CPU 14A stores the generated second clipped images in the RAM 14C.

In S105, the CPU 14A acquires feature values of the second clipped images stored in the RAM 14C in S104. The CPU 14A stores the second clipped images and the feature values of the second clipped images in association with each other in the RAM 14C.

Figure 7:
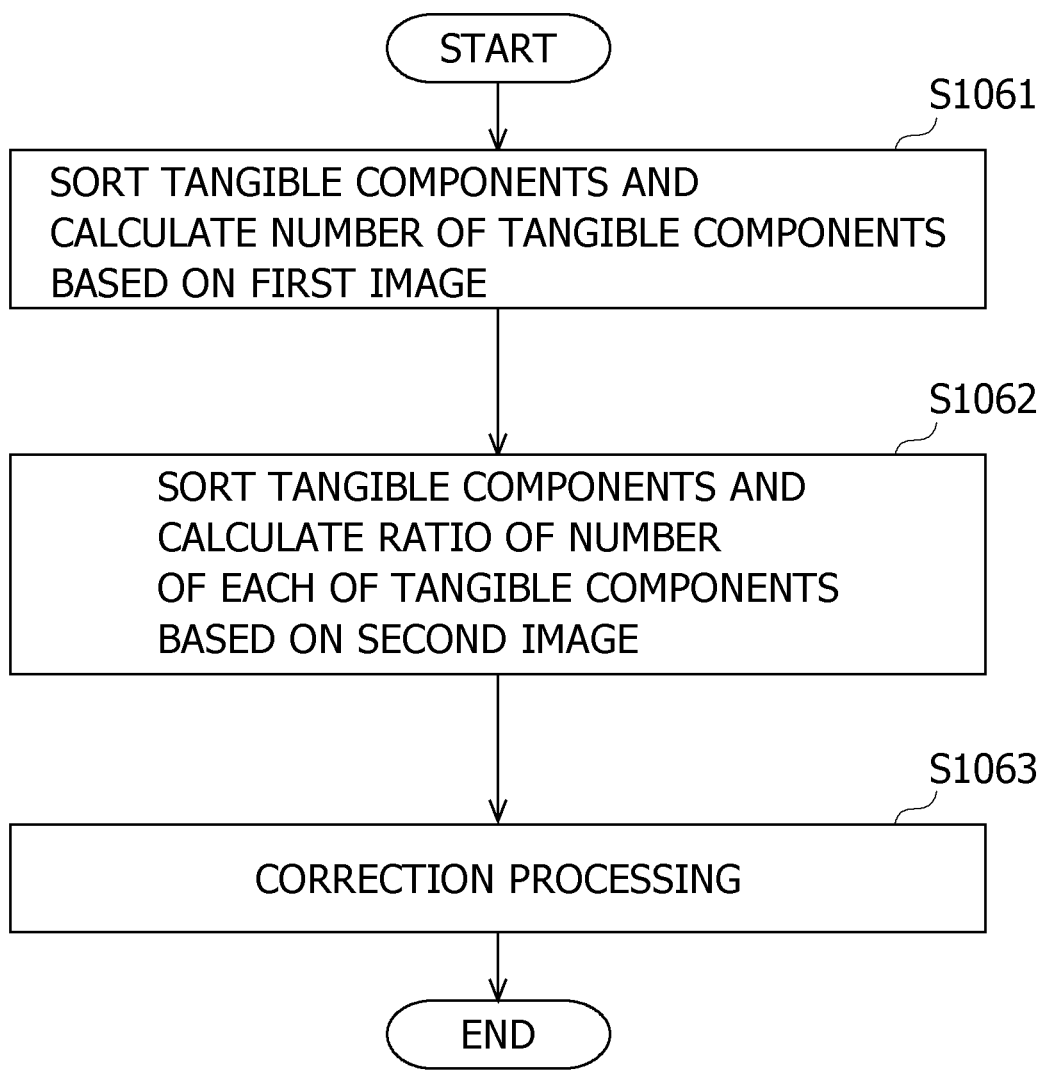
FIG. 7 is a flow chart illustrating a flow of the sorting of the tangible components and calculation of the numbers of the tangible components in the embodiment.

In S106, the CPU 14A performs the sorting of the tangible components and the calculation of the numbers of the tangible components based on the feature values acquired in S103 and S105. For the sorting, the program stored in advance in the ROM 14B is used. FIG. 7 is a flow chart illustrating a flow of the sorting of the tangible components and the calculation of the numbers of the tangible components in the embodiment. In other words, FIG. 7 illustrates a detailed flow of the processing in S106 in FIG. 6.

In S1061, the CPU 14A sorts the tangible components into the different types based on the clipped image clipped out of the first image P1, and calculates the number of each of the tangible components sorted into the different types. Specifically, the CPU 14A performs the sorting of the tangible components and the calculation of the numbers of the tangible components based on the feature values acquired in S103 in FIG. 6. FIG. 8 is a diagram illustrating an example of results of the sorting of the tangible components and the calculation of the number of the tangible components each based on the first image P1. In FIG. 8, the tangible components are sorted into large categories and into smaller category items into which the large categories are more finely sorted. For example, the tangible components are sorted into eight items "1" to "8" as the large categories. For example, in FIG. 8, epithelia in the large category "3" is more finely divided into the category items "FLAT EPITHELIUM" and "OTHER EPITHELIA". Casts in the large category "4" is more finely divided and sorted into the category items "HYALINE CAST" and "OTHER CASTS". All the large categories need not necessarily have smaller category items. As illustrated in FIG. 8, the CPU 14A calculates the number of each of the tangible components of the different types and the total number of the tangible components. It may also be possible that, in S1061, the CPU 14A calculates only the total number of the tangible components without calculating the number of each of the tangible components of the different types.

In S1062, the CPU 14A, on the basis of the second image P2, sorts the tangible components into the different types and calculates the ratio of the number of each of the tangible components sorted into the different types to the total number of the tangible components. In other words, the CPU 14A performs the sorting of the tangible components and the calculation of the ratios of the numbers of the tangible components based on the feature values acquired in S105 in FIG. 6. FIG. 9 is a diagram illustrating an example of results of the sorting of the tangible components and calculation of ratios of the numbers of the tangible components each based on the second image P2. In FIG. 9, in the same manner as in FIG. 8, the tangible components are sorted into types such as a red blood cell and a white blood cell, and the number of each of the tangible components sorted into different categories are calculated. Also, in FIG. 9, in the same manner as in FIG. 8, the tangible components are sorted into the large categories "1" to "8". As illustrated in FIG. 9, the CPU 14A calculates the number of each of the tangible components of the different types. As illustrated in FIG. 9, the CPU 14A also calculates the respective ratios of the numbers of the tangible components of the different types to the total number of the tangible components. The CPU 14A sorts the tangible component into the different types based on the second image P2 captured with a magnification higher than that with which the first image P1 is captured to be able to sort the tangible components with higher accuracy. Note that, in FIGS. 8 and 9, the tangible components are sorted into different types "RED BLOOD CELL", "WHITE BLOOD CELL", "FLAT EPITHELIUM", "OTHER EPITHELIA", "HYALINE CAST", "OTHER CASTS", "BACTERIA", "CRYSTAL", "OTHERS", AND "DUST/CELL FRAGMENT", but the sorting of the tangible components is not limited thereto.

In S1063, the CPU 14A performs correction processing. The CPU 14A corrects the numbers of the tangible components of the different types based on the total number of the tangible components acquired from the images clipped out of the first image P1, which is calculated in S1061, and the respective ratios of the numbers of the tangible components of the different types acquired from the images clipped out of the second image P2, which are calculated in S1062. FIG. 10 is a diagram illustrating a correction result obtained by performing the correction processing in the embodiment. For example, since the ratio of "RED BLOOD CELLS"

calculated in S1062 is "15.2%" and the "TOTAL NUMBER" calculated in S1061 is "82", the CPU 14A uses the total number of the individual tangible components based on the first image P1 and respective abundance ratios of the individual tangible components acquired from the second image P2 to calculate the numbers of the tangible components. By way of example, "82" as the total number of the tangible components obtained using the first image P1 is multiplied by "15.2%" as the ratio of the red blood cells sorted using the second image P2 to calculate that the number of the red blood cells after the correction is "12". The total number of the tangible components after the correction is equal to the total number of the tangible components obtained using the first image P1, and the ratio of the number of each of the tangible components in the different categories after the correction are equal to the ratios acquired from the second image P2. The CPU 14A performs such correction processing on the individual tangible components to be able to obtain the correction result illustrated in FIG. 10.

Returning back to FIG. 6, in S107 the CPU 14A outputs the correction result obtained by performing the correction processing in S106. The CPU 14A may also, e.g., output a list of the correction result illustrated in FIG. 10 as a calculation result to a monitor or to a printer to cause the printer to print the list. The CPU 14A may also output, as a calculation result, a complete component image which is produced for overall observation by randomly disposing, on a screen, the clipped images of the individual components on the basis of the number of each of the tangible components of the different types calculated in S106, an amount of the specimen used for the measurement, and magnifications and image sizes of the images displayed as the complete component image. The CPU 14A that performs the processing in S102 to S107 is an example of the "calculation unit". The processing in S102 to S107 is an example of a "calculation step".

The CPU 14A produces the complete component image in which, e.g., the first clipped images or the second clipped images the number of which is equal to the number calculated in S106 are randomly disposed in no-overlapping relation. The CPU 14A may also enlarge a portion of the complete component image and output an enlarged image which allows the shapes of the individual tangible components to be easily visually recognized. The complete component image is obtained by changing the numbers of the tangible components of the different types in the first image P1 or the second image P2 illustrated in FIG. 5 based on a result of the calculation performed in S106.

In the embodiment, the CPU 14A corrects the numbers of the tangible components of the different types based on the total number of the tangible components calculated based on the first image P1 in S1061 and on the respective ratios of the numbers of the tangible components of the different types calculated based on the second image P2 in S1062. By combining a result of a high-magnification image appropriate for counting of the numbers of the tangible components and a result of a low-magnification image appropriate for sorting of the types of the tangible components, the measurement device 20 can increase the accuracy of calculating the numbers of the tangible components of the different types. In addition, when the first image and the second image, which are different in image-capturing magnification, are acquired, only one light source 12 and only one objective lens 101 are required. This allows the sorting of the tangible components in the specimen and the calculation of the numbers of the tangible components to be accomplished with lower cost.

In the embodiment, the CPU 14A outputs the complete component image in which the first clipped images or the second clipped images the number of which corresponds to the number calculated in S106 are randomly disposed in no-overlapping relation. In the embodiment, the CPU 14A may also enlarge a portion of the complete component image and output an enlarged image which allows the respective shapes of the tangible components to be easily visually recognized. Thus, the embodiment allows easy visual recognition of the types of the tangible components in the urine and the number of the tangible components in the urine.

In the embodiment, the first camera 105A and the second camera 105B have the same focal positions on the respective optical axes thereof. Accordingly, the first image P1 and the second image P2 are different in magnification. The first image P1 can be captured to cover a wide range, but is lower in the accuracy of sorting the tangible components than the second image P2. In the embodiment, the numbers of the individual tangible components are calculated using the number of the tangible components calculated using the first image P1 and the abundance ratios of the tangible components in the different categories calculated using the second image P2 to allow the accuracy of counting the numbers of the tangible components of the different types to be increased.

First Modification

In the embodiment, based on the total number of the tangible components calculated based on the first image P1 and on the respective ratios of the numbers of the tangible components of the different types calculated based on the second image P2, the numbers of the tangible components of the different types are corrected for all the large categories. In a first modification, a description will be given of processing of correcting the numbers of the tangible components in the specified large category. In the first modification, the processing illustrating in FIG. 7 of the embodiment is modified. Information representing the large category to be specified may be, e.g., stored in advance in the ROM 14B or the large category to be specified may be selected by an operation by a user. Components common to the embodiment are denoted by the same reference numerals, and a description thereof is omitted. Referring to the drawings, a description will be given below of the first modification.

Figure 11:
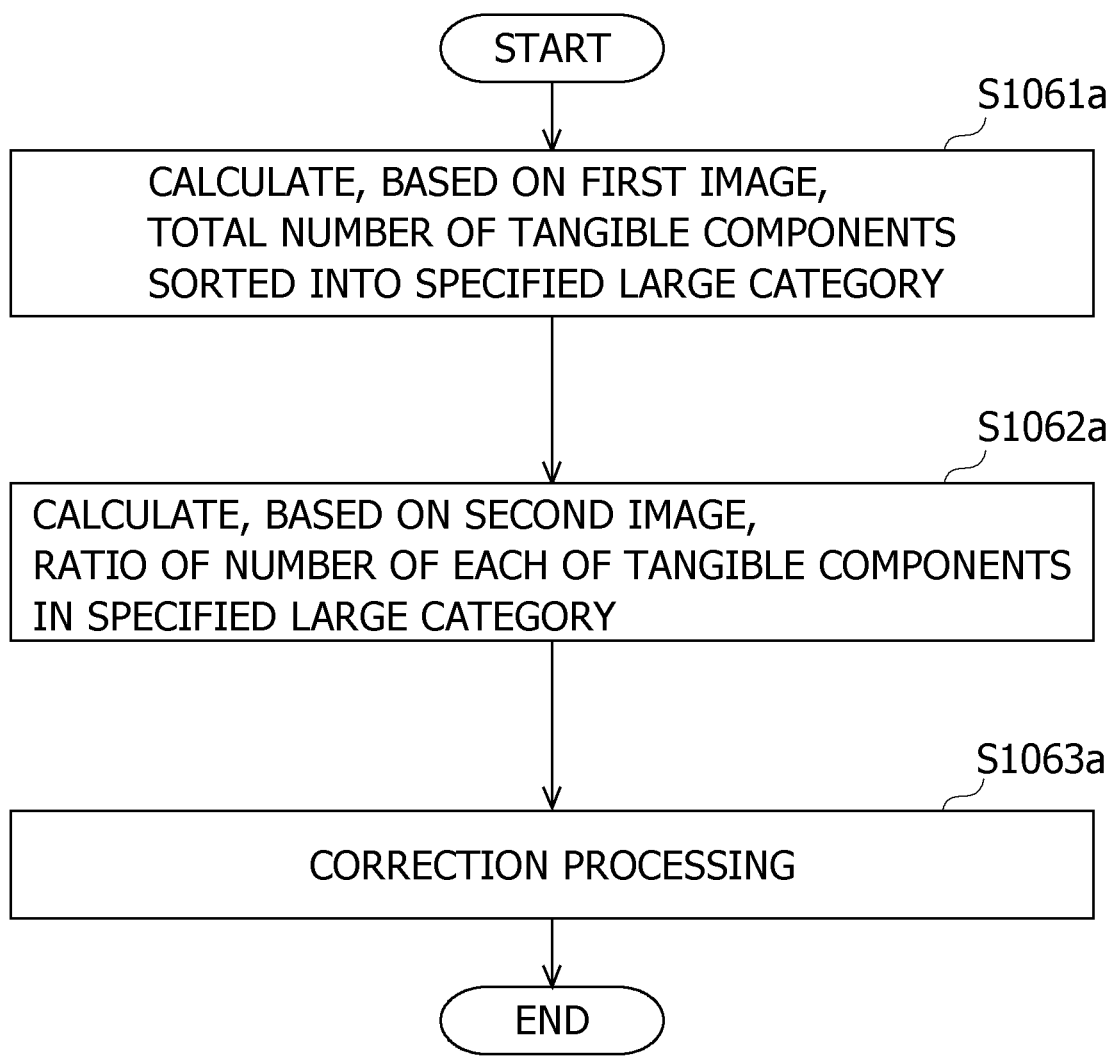
FIG. 11 is a flow chart illustrating a flow of the sorting of the tangible components and the calculation of the numbers of the tangible components in a first modification.

FIG. 11 is a flow chart illustrating a flow of the sorting of the tangible components and the calculation of the numbers of the tangible components in the first modification. The epithelia as the large category "3" are specified herein. In S1061a, the CPU 14A calculates, based on the first image P1, the total number of the tangible components sorted into the epithelia as the specified large category "3". It is assumed herein that results of the sorting of the tangible components and the calculation of the number of the tangible components each based on the first image P1 are in a state illustrated in FIG. 8 and the specified large category is the epithelia "3". The CPU 14A adds up "12" as the number of the tangible components in "FLAT EPITHELIUM" sorted into the epithelia as the large category "3" and "1" as the number of the tangible components in "OTHER EPITHELIA" to calculate the total number "13". The CPU 14A that performs the processing in S1061a is an example of a "first calculation unit".

Figure 12:
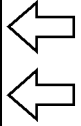
FIG. 12 is a diagram illustrating an example of the results of the sorting of the tangible components and the ratios of the numbers of the tangible components each based on the second image.

In S1062a, the CPU 14A, on the basis of the second image P2, calculates the ratio of the number of each of the individual tangible components sorted into the epithelia as the specified large category "3". FIG. 12 is a diagram illustrating an example of the results of the sorting of the tangible components and the calculation of the ratios of the numbers of the tangible components each based on the second image P2. The CPU 14A adds up "8" as the number of the tangible components in "FLAT EPITHELIUM" sorted into the epithelia as the large category "3" and "2" as the number of the tangible components in "OTHER EPITHELIA" to calculate that the total number of the tangible components sorted into the large category "3" is "10". The CPU 14A calculates, based on the total number of the tangible components sorted into the large category "3" which is calculated based on the second image P2 and on the number of each of the tangible components in "FLAT EPITHELIUM" and "OTHER EPITHELIA", "80.0%" as a ratio of "FLAT EPITHELIUM" and "20.0%" as a ratio of "OTHER EPITHELIA" in the large category "3". The CPU 14A that performs the processing in S1062a is an example of a "second calculation unit".

In S1063a, the CPU 14A corrects the number of each of the tangible components in "FLAT EPITHELIUM" and "OTHER EPITHELIA" based on the total number of the tangible components sorted into the epithelia as the large category "3", which is calculated based on the first image P1 in S1061a, and on the respective ratios of "FLAT EPITHELIUM" and "OTHER EPITHELIA" as category items, which are calculated based on the second image P2 in S1062a. The CPU 14A multiplies "13" as the total number of the tangible components sorted into the large category "3", which is calculated based on the first image P1, by "80%" as the ratio of "FLAT EPITHELIUM", which is calculated based on the second image P2, to calculate that a corrected value of the number of the tangible components in "FLAT EPITHELIUM" is "10". The CPU 14A also multiplies "13" as the total number of the tangible components sorted into the large category "3", which is calculated based on the first image P1, by "20%" as the ratio of "OTHER EPITHELIA", which is calculated based on the second image P2, to calculate that "3" is a corrected value of the number of the tangible components in "OTHER EPITHELIA". The total number of the tangible components after the correction is equal to the total number of the tangible components obtained using the first image P1. It may also be possible to subtract, from the total number of the tangible components included in the specified large category, the number of the tangible components included in another category item after the correction and thus calculate the number of the tangible components in the category item after the correction. In the example described above, it may also be possible to subtract, from the total number 13 of the tangible components included in the epithelia, 10 as the number of the tangible components in "FLAT EPITHELIUM" after the correction to calculate that the number of the tangible components in "OTHER EPITHELIA" after the correction is "3", and vice versa. The CPU 14A performs such correction processing on each of the tangible components sorted into the specified large category to be able to obtain a correction result illustrated in FIG. 13.

According to the first modification, it is possible to accurately calculate the number of the tangible components in the specified large category and also reduce the processing load on the CPU 14A compared to that in the embodiment in which the correction processing is performed for all the large categories. Note that, in the first modification, a case where all the categories are specified corresponds to the embodiment described above.

Second Modification

In a second modification, in the sorting of the tangible components based on the first image P1, the large category prone to erroneous sorting is specified, and correction is performed for the specified category. In the second modification, the processing illustrated in FIG. 7 of the embodiment is modified. Information specifying the large category prone to erroneous sorting may be, e.g., stored in advance in the ROM 14B or, alternatively, the large category to be specified may be selected by an operation by the user. Components common to the embodiment are denoted by the same reference numerals, and a description thereof is omitted. Referring to the drawings, a description will be given below of the second modification.

Figure 14:
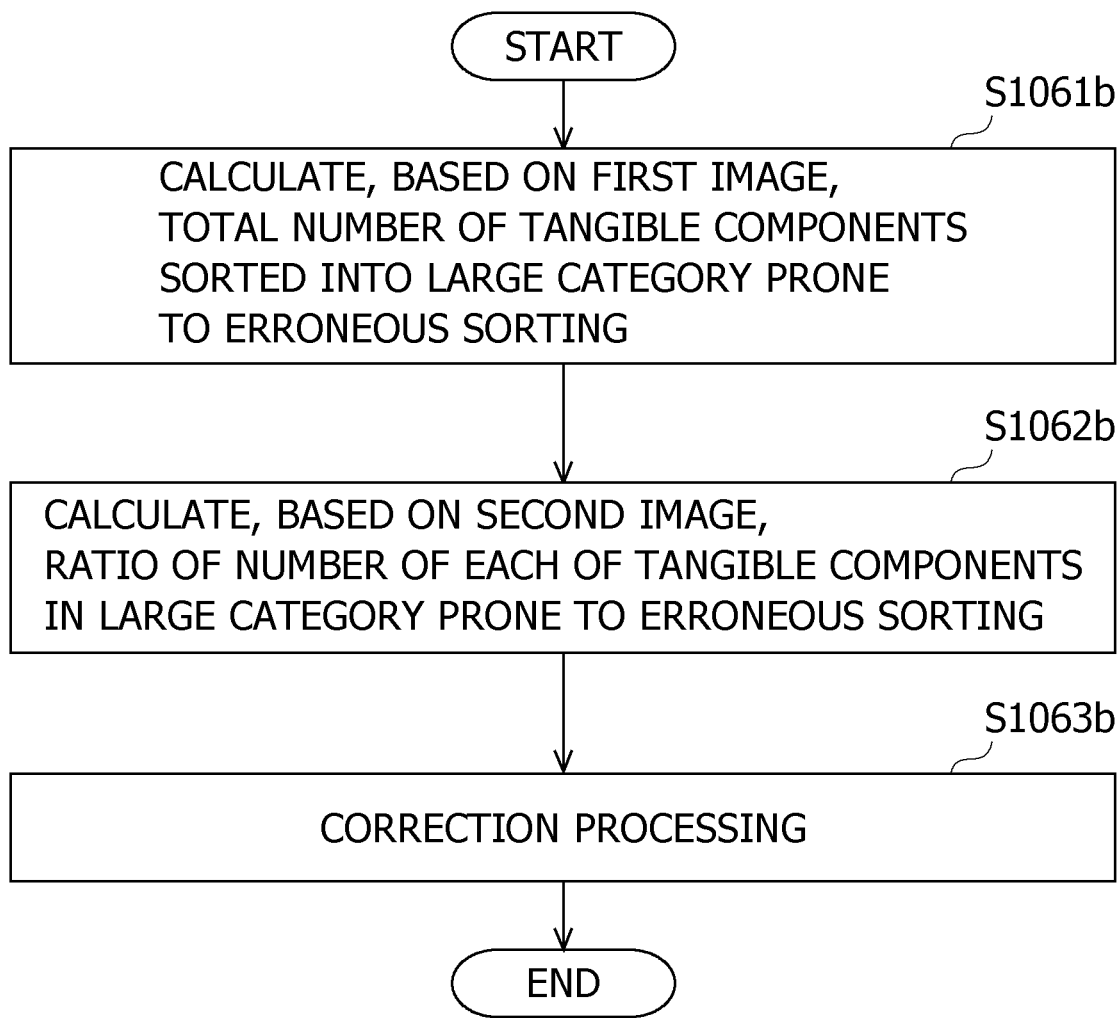
FIG. 14 is a flow chart illustrating a flow of the sorting of the tangible components and the calculation of the numbers of the tangible components in a second modification.

FIG. 14 is a flow chart illustrating a flow of the sorting of the tangible components and the calculation of the number of the tangible components in the second modification. In S1061b, the CPU 14A calculates, from the result of the sorting of the tangible components based on the first image P1, the total number of the tangible components sorted into the large categories prone to erroneous sorting. It is assumed herein that the results of the sorting of the tangible components and the calculation of the number of the tangible components each based on the first image P1 are in a state illustrated in FIG. 8, and the large categories specified as the large categories prone to erroneous sorting are "1", "5", "6", and "8". The CPU 14A calculates that the total number of the tangible components sorted into "RED BLOOD CELL", "BACTERIA", "CRYSTAL", and "DUST/CELL FRAGMENT" serving as the tangible components sorted into the large categories "1", "5", "6", and "8" by using the first image P1 is "64". The CPU 14A that performs the processing in S1061b is an example of the "first calculation unit".

Figure 15:
FIG. 15 is a diagram illustrating an example of the results of the sorting of the tangible components and the ratios of the numbers of the tangible components each based on the second image.

In S1062b, the CPU 14A calculates, from the result of the sorting of the tangible components based on the second image P2, respective ratios of the numbers of the tangible components in the large categories prone to erroneous sorting. FIG. 15 is a diagram illustrating an example of the results of the sorting of the tangible components and the ratios of the numbers of the tangible components each based on the second image P2. The CPU 14A clips the tangible components out of the second image P2 and calculates the total number of the category items (tangible components) sorted into the large categories "1", "5", "6", and "8". The CPU 14A calculates herein that the total number of the tangible components in "RED BLOOD CELL", "BACTERIA", "CRYSTAL", and "DUST/CELL FRAGMENT" is "49". The CPU 14A calculates the respective ratios of the numbers of the tangible components in "RED BLOOD CELL", "BACTERIA", "CRYSTAL", and "DUST/CELL FRAGMENT" to the calculated total number. For example, the CPU 14A divides "10" as the number of the tangible components in "RED BLOOD CELL" by "49" as the total number of the tangible components included in the specified categories to calculate that the ratio of the number of the tangible components in "RED BLOOD CELL" is "20.4%". The CPU 14A that performs the processing in S1062b is an example of the "second calculation unit".

Figure 16:
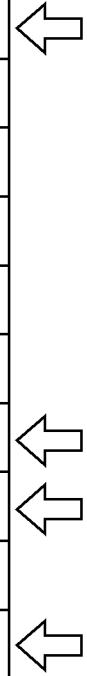
FIG. 16 is a diagram illustrating an example of the correction result obtained by performing the correction processing in a second modification.

In S1063b, the CPU 14A corrects the number of each of the tangible components sorted into the large categories prone to erroneous sorting based on the total number calculated using the first image P1 in S1061b and on the respective ratios of the numbers of the tangible components calculated from the second image P2 in S1062b. FIG. 16 is a diagram illustrating an example of a correction result obtained by performing correction processing in the second modification. For example, the CPU 14A multiplies "20.4%" as the ratio of the number of the tangible components in "RED BLOOD CELL" calculated from the second image P2 by "64" as the total number of the tangible components sorted into "1", "5", "6", and "8" as the large categories prone to erroneous sorting in the first image P1 to calculate that the number of the red blood cells after the correction is "13". The CPU 14A performs such correction processing on the individual tangible components classified into the large categories prone to erroneous sorting to be able to obtain the correction result illustrated in FIG. 16. The total number of the tangible components after the correction is equal to the total number of the tangible components obtained using the first image P1.

According to the second modification, it is possible to accurately calculate the number of the tangible components in the large categories prone to erroneous sorting and also reduce the processing load on the CPU 14A compared to that in the embodiment in which the correction processing is performed for all the large categories.

Third Modification

By being based on the second image P2 that is captured with a high image-capturing magnification, it is possible to more particularly and accurately sort the tangible components than by being based on the first image P1. In a third modification, a description will be given of processing which allows sorting of the tangible components in more detail by using the second image P2 than sorting of the tangible components by using the first image P1 is used. In the third modification, the processing illustrated in FIG. 7 of the embodiment is modified. Components common to the embodiment are denoted by the same reference numerals, and a description thereof is omitted. Referring to the drawings, a description will be given below of the third modification.

Figure 17:
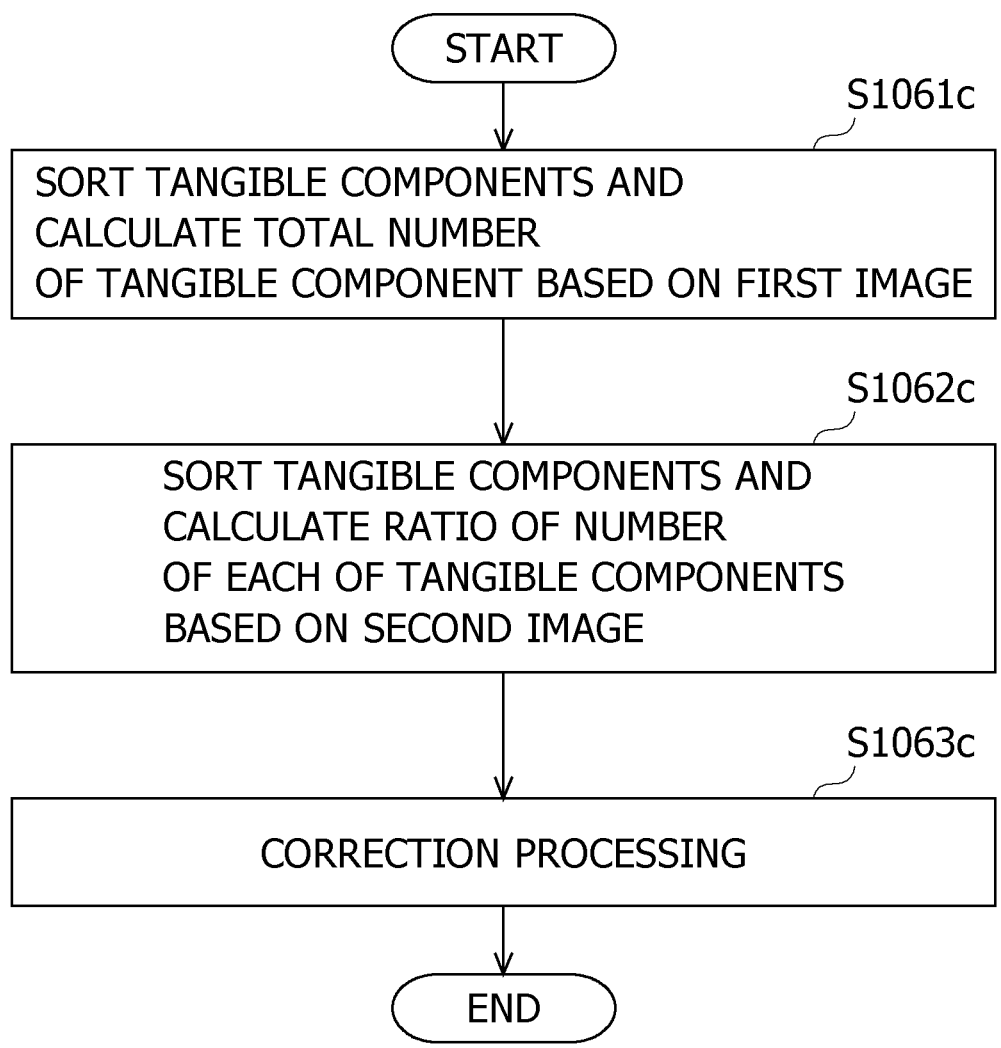
FIG. 17 is a flow chart illustrating a flow of the sorting of the tangible components and the calculation of the numbers of the tangible components in a third modification.

FIG. 17 is a flow chart illustrating a flow of the sorting of the tangible components and the calculation of the number of the tangible components in the third modification. In S1061c, the CPU 14A performs the sorting of the tangible components and the calculation of the total number of the tangible components based on the first image P1. FIG. 18 is a diagram illustrating an example of the results of the sorting of the tangible components and the calculation of the number of the tangible components each based on the first image P1 in the third modification. It is assumed that, in S1061c, as illustrated in FIG. 18, the tangible components are sorted into eight types "RED BLOOD CELL", "WHITE BLOOD CELL", "EPITHELIUM", "CAST", "BACTERIA", "CRYSTAL", "OTHERS", and "DUST/CELL FRAGMENT". It is also assumed that, as the "TOTAL NUMBER" of the tangible components, "101" is obtained. The CPU 14A that performs the processing in S1061c is an example of the "first calculation unit".

In S1062c, the CPU 14A performs the sorting of the tangible components and the calculation of the respective ratios of the numbers of the tangible components based on the second image P2. FIG. 19 is a diagram illustrating an example of the results of the sorting of the tangible components and the calculation of the ratios of the numbers of the tangible components each based on the second image P2 in the third modification. In the third modification, by taking advantage of the high magnification of the second image P2, the tangible components are more particularly and finely sorted than are sorted based on the first image P1 in S1061c. For example, the tangible components sorted into "RED BLOOD CELL" in the sorting in S1061c are sorted into two types of category items "ISOMORPHIC RED BLOOD CELL" and "DYSMORPHIC RED BLOOD CELL" in the sorting in S1062c. The CPU 14A also calculates a ratio of the number of each of the sorted tangible components. For example, since the "TOTAL NUMBER" of the tangible components detected based on the second image P2 is "80" and the "NUMBER" of the tangible components in "ISOMORPHIC RED BLOOD CELL" is "8", the CPU 14A calculates that the "RATIO" of the number of the tangible components in "ISOMORPHIC RED BLOOD CELL" is "10.0%". The CPU 14A that performs the processing in S1062c is an example of the "second calculation unit".

In S1063c, the CPU 14A calculates the number of each of the individual tangible components based on the total number of the tangible components calculated based on the first image P1 in S1061c and on the respective ratios of the numbers of the tangible components particularly sorted based on the second image P2 in S1062c. FIG. 20 is a diagram illustrating a correction result obtained by performing the correction processing in the third modification. For example, the CPU 14A calculates that the number of the tangible components in "ISOMORPHIC RED BLOOD CELL" after the correction is "10" based on "10.0%" as the ratio of the number of the tangible components in "ISOMORPHIC RED BLOOD CELLS" calculated in S1062c to "101" as the total number calculated in S1061c. The CPU 14A performs such correction processing on the individual tangible components to be able to obtain the correction result illustrated in FIG. 20.

In the third modification, even the tangible components of the types hard to sort using the first image P1 are sorted based on the second image P2, and the number of each of the tangible components of the different types sorted based on the second image P2 are corrected based on the total number calculated based on the first image P1. According to the third modification, it is possible to accurately calculate the numbers of even the tangible components of the types hard to sort using the first image P1. Note that, in the third modification, all the categories are specified, and correction is performed in all the categories.

Other Modifications

In each of the embodiment and the modifications described above, the image-capturing range of the second image P2 is a portion of the image-capturing range of the first image P1. However, the image-capturing range of the second image P2 might not be included in the image-capturing range of the first image P1. For example, the image-capturing range of the first image P1 may be disposed upstream or downstream of the image-capturing range of the second image P2. Even when the image-capturing range of the second image P2 is not included in the image-capturing range of the first image P1, the number of the tangible components included in the specified category can be calculated by using the same method as that described above.

In each of the embodiment and the modifications described above, the image-capturing device 1 performs image-capturing in a bright field, but the image-capturing device 1 may also perform image-capturing in a dark field or with a phase difference, differential interference, polarization, fluorescence, or the like. For example, when image-capturing is performed in the dark field, it is appropriate to illuminate the flow cell 13A with the light from the light source 12 and cause reflected light from the flow cell 13A to be incident on the objective lens 101.

In each of the embodiment and the modifications described above, the image-capturing device 1 includes the second image capturing unit 100B that performs image-capturing with the second magnification higher than the first magnification. However, the image-capturing device 1 may also include two or more image capturing units that perform image-capturing with a magnification higher than the first magnification. In this case, the image-capturing ranges of the image capturing units that perform image-capturing with the magnifications higher than the first magnification are preferably included in the image-capturing range in which the first image capturing unit 100A performs image-capturing. In other words, the image capturing units that perform image-capturing with the magnifications higher than the first magnification preferably image-captures an enlarged image of a local region of the image captured by the first image capturing unit 100A.

The embodiment and the modifications each disclosed above can be combined with each other.

What is claimed is:

1. A measurement device comprising:
   a first image capturing unit configured to obtain a first image by image-capturing liquid containing tangible components;
   a second image capturing unit having an image-capturing magnification higher than that of the first image capturing unit and which is configured to obtain a second image by image-capturing the liquid containing tangible components simultaneously with the first image capturing unit; and
   a calculation unit configured to:
      clip the tangible components from the first image and the second image,
      sort the clipped tangible components from the second image into different types, and
      calculate a total number of the tangible components clipped out from the first image, a ratio of a number of each of the tangible components of the different types clipped out from the second image to a total number of the tangible components clipped out from the second image and then the number of each type of the tangible components in the first image based on the total number of the tangible components clipped out from the first image and the ratio of a number of each of the tangible components of the different types.

2. The measurement device according to claim 1, wherein an image-capturing range of the second image is a portion of an image-capturing range of the first image.

3. The measurement device according to claim 1, wherein the calculation unit multiplies the total number of the tangible components clipped out from the first image by the ratio of the number of each of the tangible components of the different types clipped out from the second image, thereby calculating the number of the tangible components.

4. The measurement device according to claim 1, wherein the calculation unit outputs a complete component image in which the clipped images respectively representing the tangible components of the different types are disposed based on the number of each of the tangible components of the different types calculated.

5. The measurement device according to claim 1, wherein
   the first image capturing unit and the second image capturing unit have same focal positions on respective optical axes thereof.

6. A measurement method comprising:
   obtaining a first image by image-capturing liquid containing tangible components;
   clipping the tangible components from the first image;
   calculating a total number of the tangible components clipped out from the first image;
   obtaining a second image by image-capturing the liquid containing the tangible components at the same time as the first image is captured, the second image having an image-capturing magnification higher than that of the first image;
   clipping the tangible components from the second image;
   sorting the clipped tangible components from the second image into different types;
   calculating a ratio of a number of each of the tangible components sorted into the different types clipped out from the second image to a total number of the tangible components clipped out from the second image; and
   calculating the number of each type of the tangible components in the first image based on the total number of the tangible components clipped out from the first image and the ratio of a number of each of the tangible components of the different types.

7. The measurement method according to claim 6, wherein an image-capturing range of the second image is a portion of an image-capturing range of the first image.

\* \* \* \* \*